United States Patent [19]
Schricker

[11] Patent Number: 5,750,887
[45] Date of Patent: May 12, 1998

[54] METHOD FOR DETERMINING A REMAINING LIFE OF ENGINE OIL

[75] Inventor: David R. Schricker, Dunlap, Ill.

[73] Assignee: Caterpillar Inc., Peoria, Ill.

[21] Appl. No.: 749,603

[22] Filed: Nov. 18, 1996

[51] Int. Cl.$^6$ ............................ B60Q 1/00; G01M 15/00; G01D 21/00
[52] U.S. Cl. .................. 73/117.3; 73/118.1; 340/438; 340/439; 364/431.03; 364/550
[58] Field of Search .................................. 73/116, 117.2, 73/117.3, 118.1; 364/431.03, 550; 340/438, 439

[56] References Cited

U.S. PATENT DOCUMENTS

| | | | |
|---|---|---|---|
| 3,903,736 | 9/1975 | Bissett et al. | 73/117.3 |
| 4,311,041 | 1/1982 | Reid et al. | 73/117.3 |
| 4,495,417 | 1/1985 | Hohensang | 250/343 |
| 4,497,200 | 2/1985 | Tournier | 73/117.3 |
| 4,506,337 | 3/1985 | Yasuhara | 73/117.3 |
| 4,533,900 | 8/1985 | Muhlberger et al. | 73/117.3 |
| 4,677,847 | 7/1987 | Sawatari et al. | 73/117.3 |
| 4,739,482 | 4/1988 | Wrigge | 73/117.3 |
| 4,742,476 | 5/1988 | Schwartz et al. | 364/550 |
| 4,796,204 | 1/1989 | Inoue | 73/117.3 |
| 4,839,831 | 6/1989 | Imajo et al. | 73/117.3 |
| 4,847,768 | 7/1989 | Schwartz et al. | 364/424.03 |
| 4,884,054 | 11/1989 | Moon, Sr. | 73/117.3 |

OTHER PUBLICATIONS

"BMW 540; 6–Speed Manual Standard & Optional Features", from BMW of North America internet site (www.bmwusa.com), describing, Service Interval Indicator.

SAE Technical Paper Series 870403,1987, Development of an Automatic Engine Oil–Change Indicator System/Shirley Schwartz, Donald Smolenski.

Primary Examiner—George M. Dombroske
Attorney, Agent, or Firm—James R. Yee; David M. Masterson

[57] ABSTRACT

A method for determining a remaining life of engine oil in an engine is provided. The method includes the steps of measuring a plurality of engine parameters, determining an estimate of the characteristics of the engine oil as a function of the engine parameters, and trending the estimate and responsively determining the remaining life of the engine oil.

30 Claims, 6 Drawing Sheets

Fig_1_
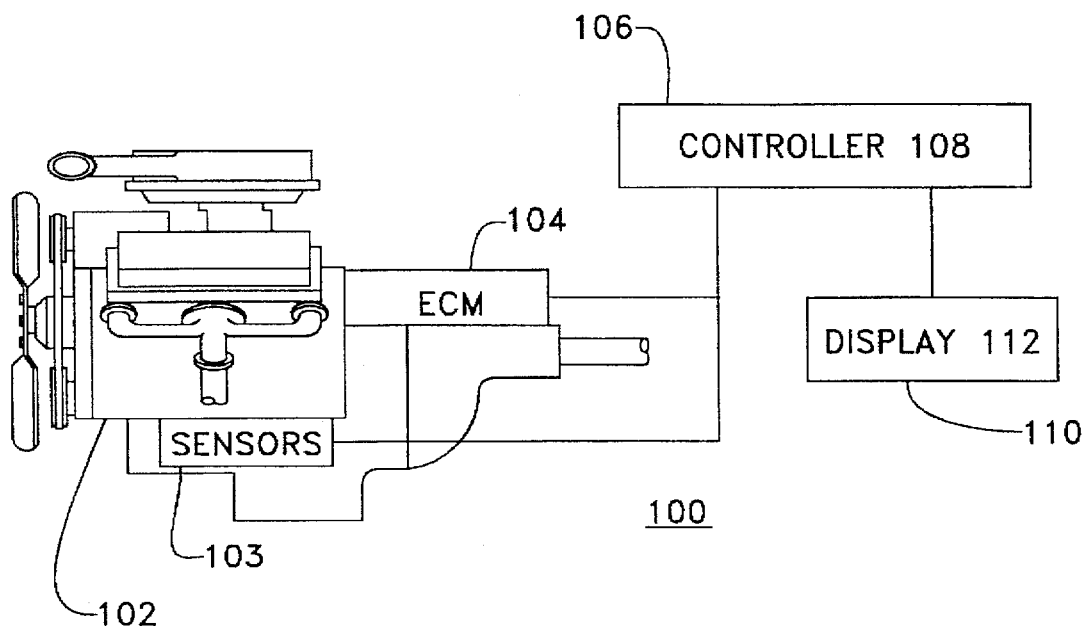
Fig_2_
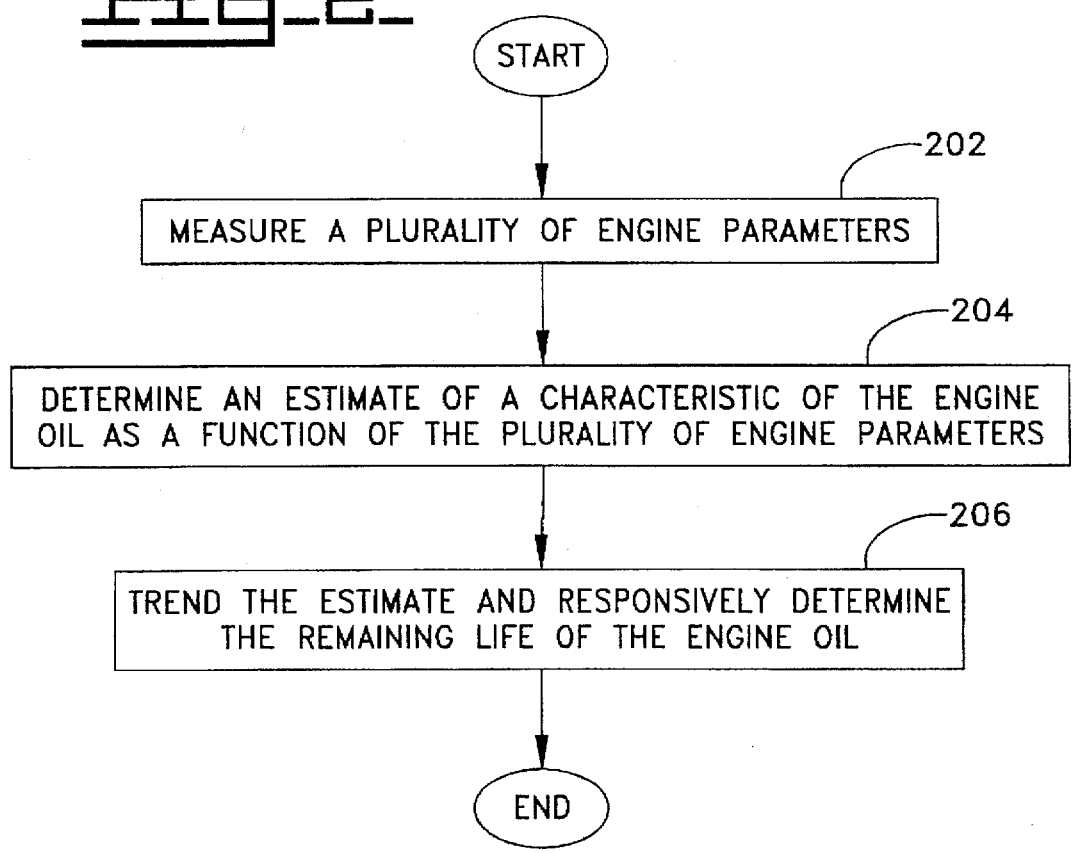

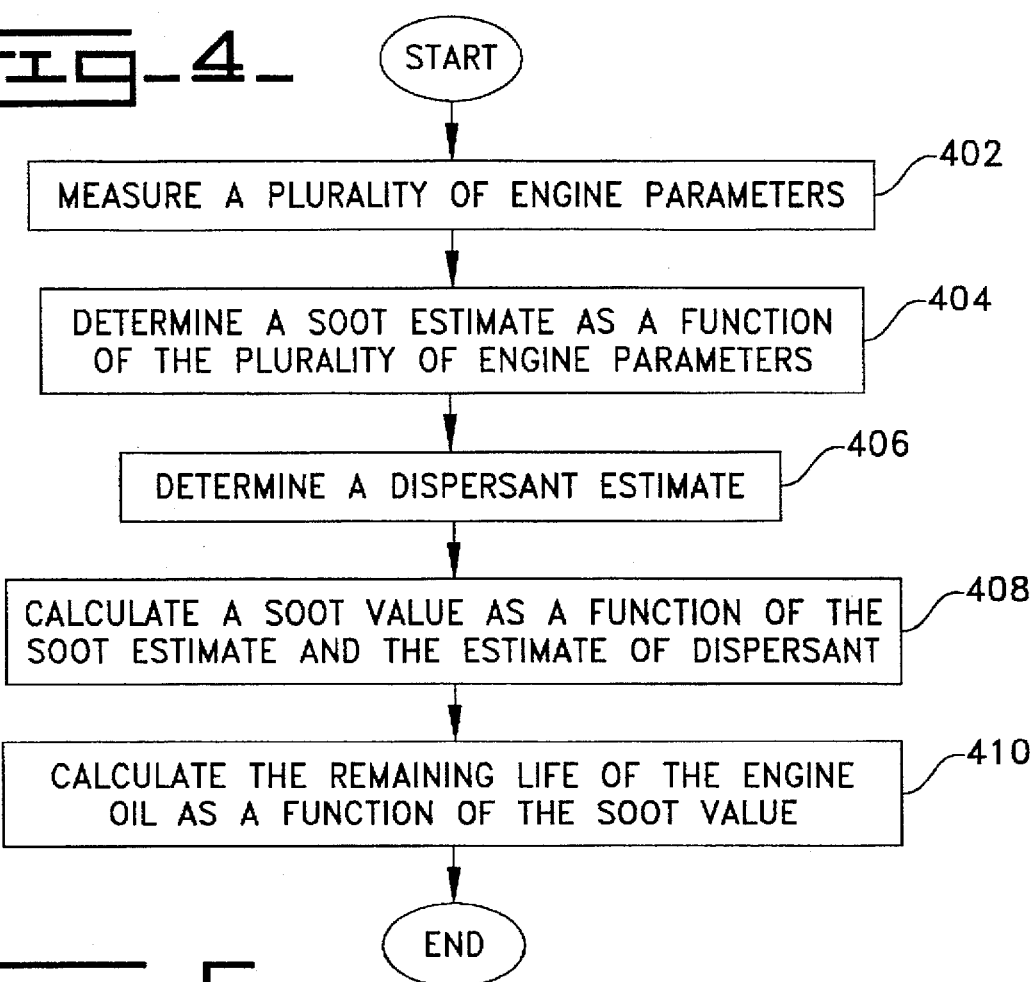
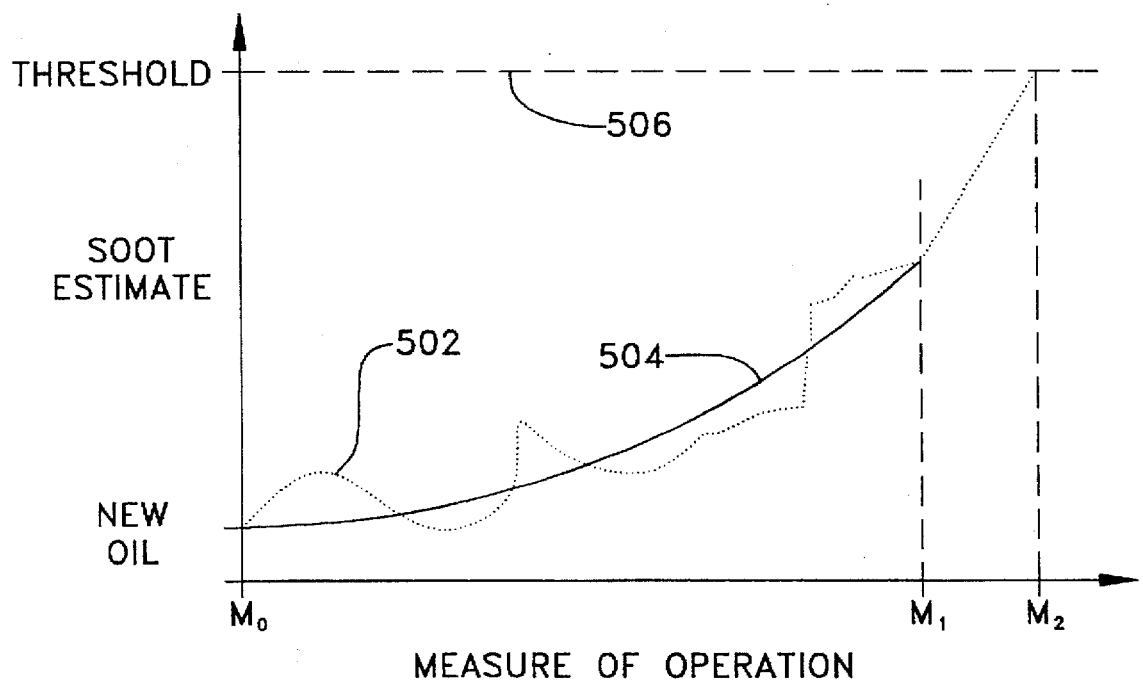

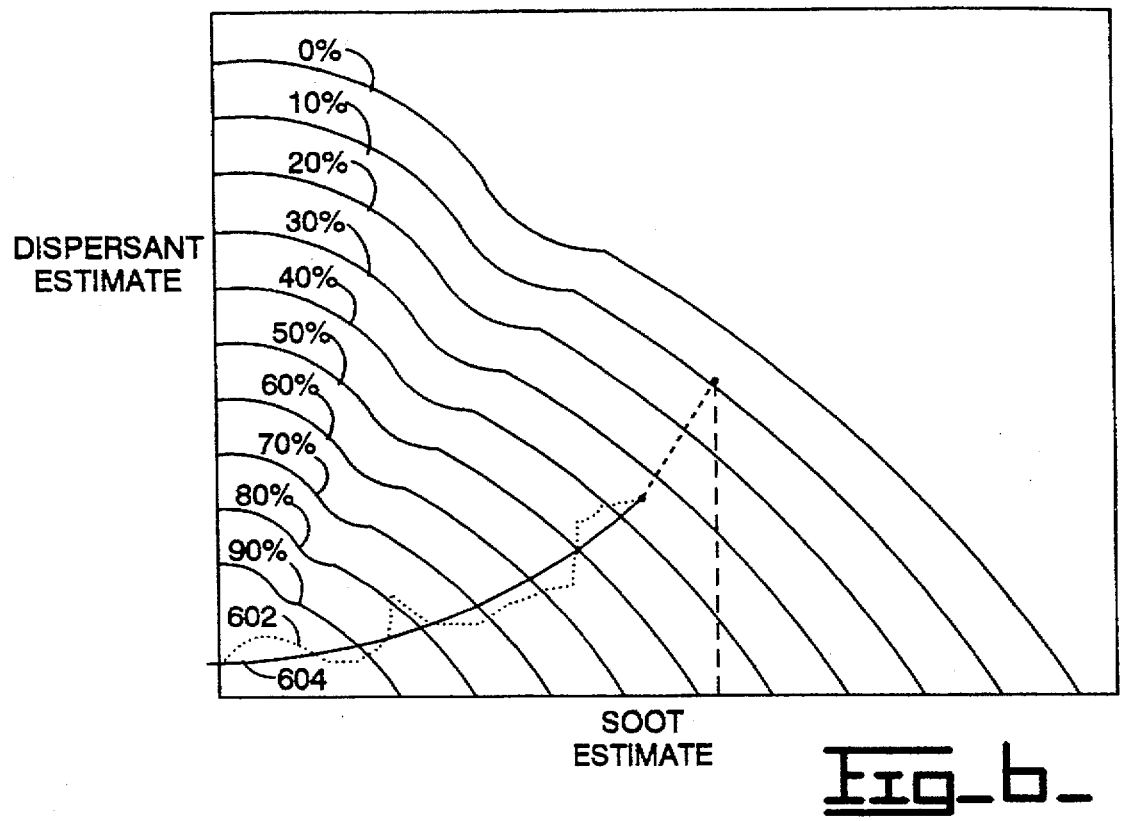
Fig_6_
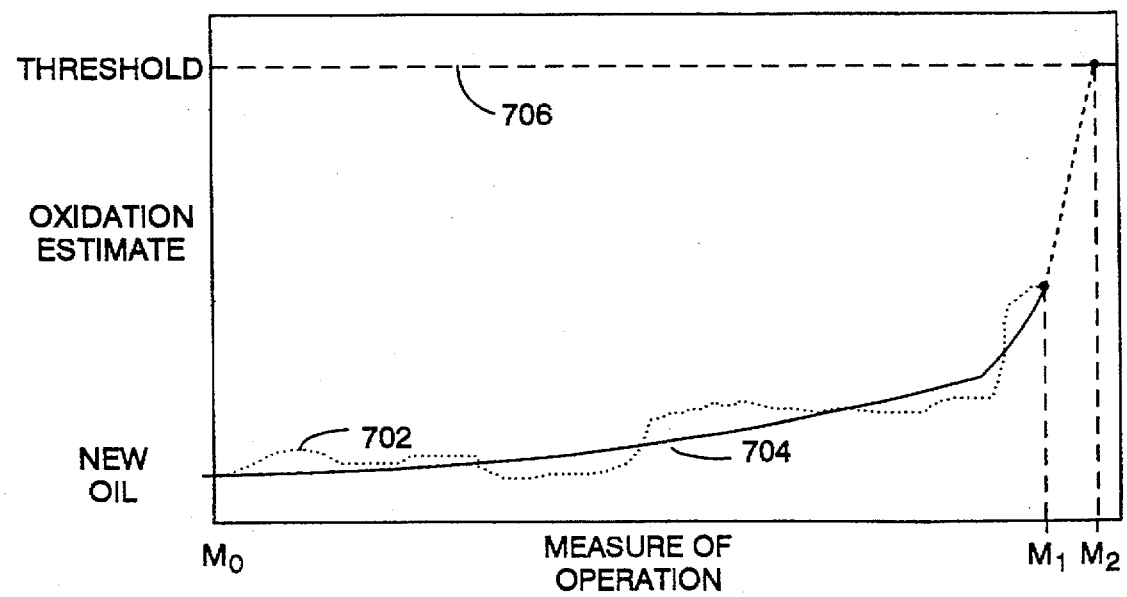
Fig_7_

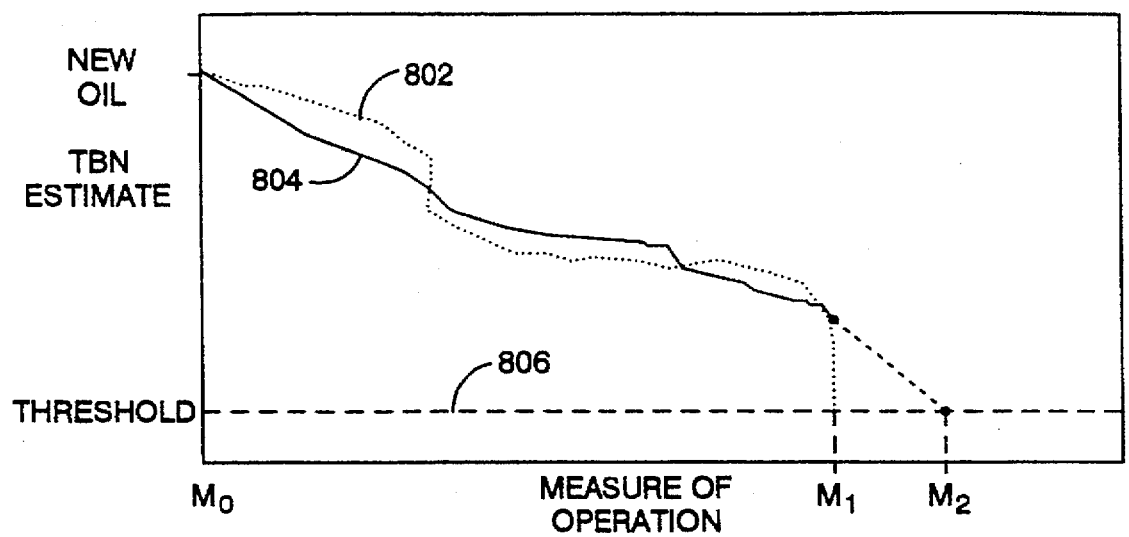
Fig_8_
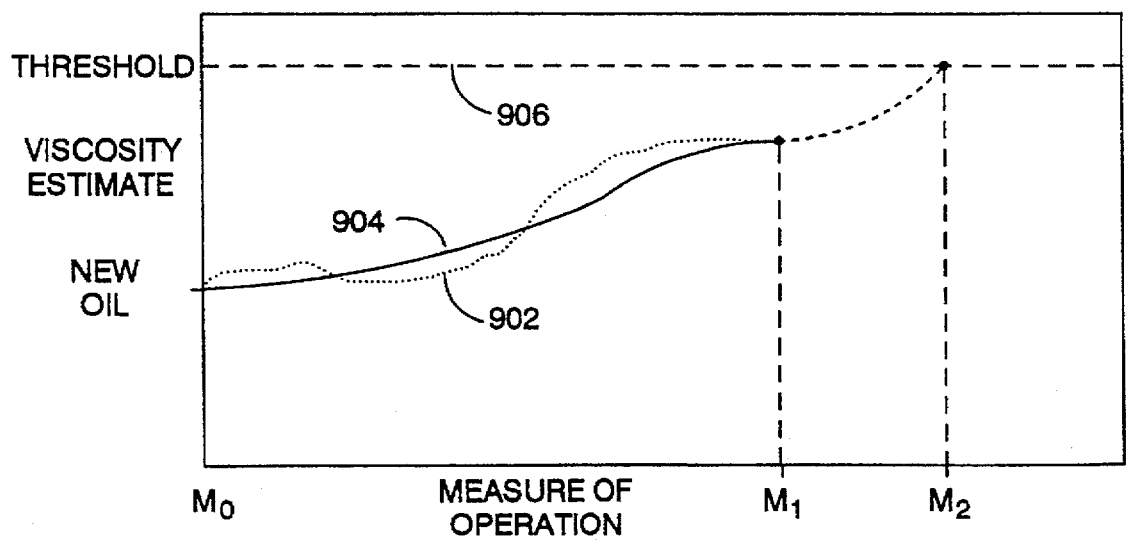
Fig_9_

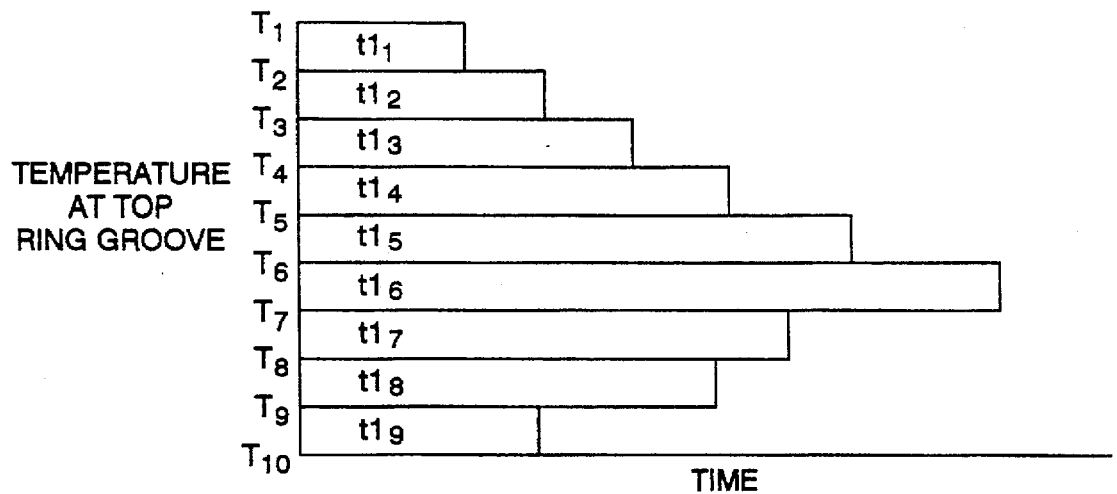
Fig-10-
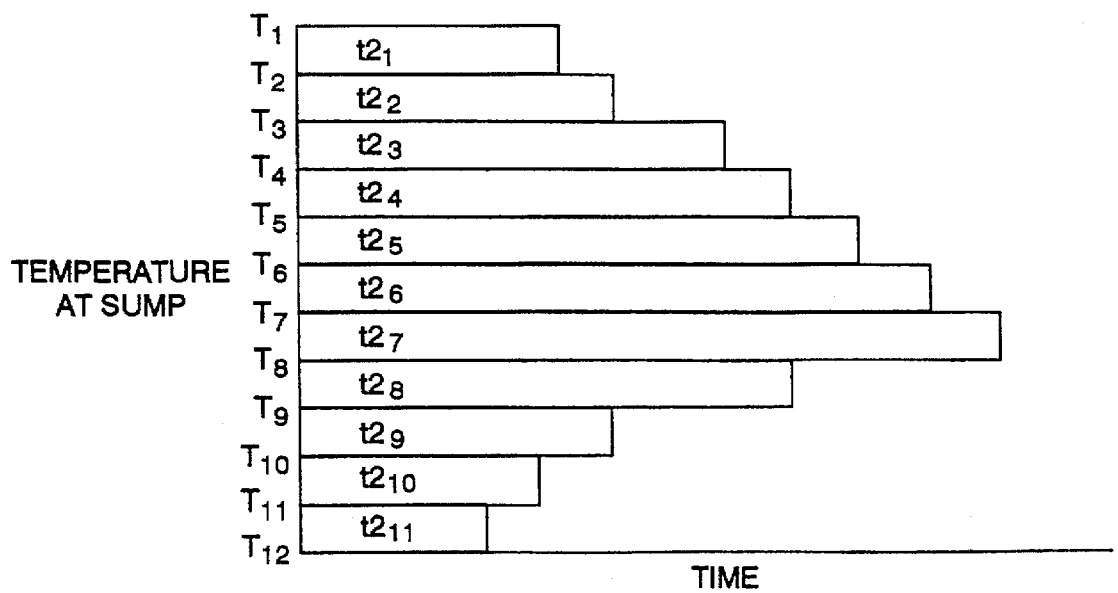
Fig-11-

5,750,887

METHOD FOR DETERMINING A REMAINING LIFE OF ENGINE OIL

TECHNICAL FIELD

The present invention relates generally to engine oil and, more particularly, to a method for determining a remaining life of engine oil in an engine.

BACKGROUND ART

Changing engine oil is one of the key processes used in extending engine life. Generally, the oil in an engine is changed in accordance with a set schedule. The schedule is based on an estimate of the life of the oil under a worst case scenario. Thus, the schedule may require changing the oil prematurely.

The present invention is aimed at solving one or more of the problems identified above.

DISCLOSURE OF THE INVENTION

In one aspect of the present invention, a method for determining a remaining life of engine oil in an engine is provided. The method includes the steps of measuring a plurality of engine parameters, determining an estimate of the characteristics of the engine oil as a function of the engine parameters, and trending the estimate and responsively determining remaining life of the engine oil.

In another aspect of the present invention, a method for determining the remaining life of engine oil in an engine is provided. The method includes the steps of measuring a plurality of engine parameters, determining an estimate of a first characteristic of the engine oil as a function of the engine parameters, and determining an estimate of a second characteristic of the engine oil as a function of the engine parameters. First and second estimates of the remaining life of the engine oil are calculated as a function of the estimate of the first characteristic and the estimate of the second characteristic, respectively. The first and second estimate of the remaining life are compared and the remaining life is responsively determined.

BRIEF DESCRIPTION OF THE DRAWINGS

FIG. 1 is a block diagram of an engine and apparatus for determining the percentage remaining life of engine oil in the engine;

FIG. 2 is a block diagram illustrating operation of a method for determining the remaining life of engine oil, according to an embodiment of the present invention;

FIG. 4 is a flow diagram illustrating a method for determining the remaining life of engine oil, according to a third embodiment of the present invention;

FIG. 5 is a graph illustrating an estimate of soot present in engine oil versus a measure of operation;

FIG. 6 is a graph illustrating an estimate of the soot present in engine oil versus an estimate of dispersant;

FIG. 7 is a graph illustrating an estimate of the level of oxidation of engine oil versus a measure of operation;

FIG. 8 is a graph illustrating an estimate of total base number versus a measure of operation;

FIG. 9 is a graph illustrating an estimate of viscosity of engine oil versus a measure of operation;

FIG. 10 is a histogram of a temperature at top ring groove of an engine versus time; and FIG. 11 is a histogram of temperature at sump versus time.

BEST MODE FOR CARRYING OUT THE INVENTION

Figure 3:
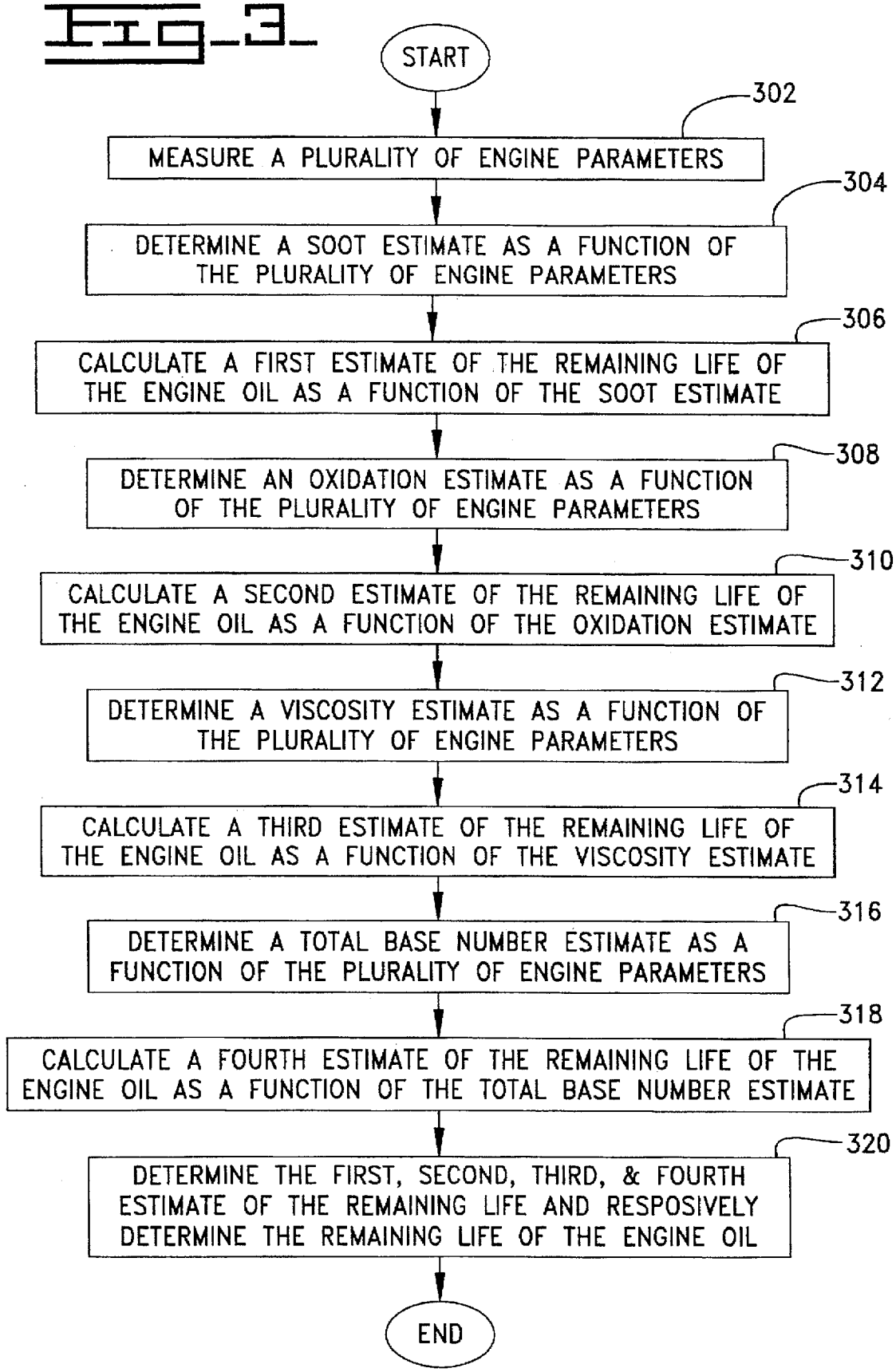
FIG. 3 is a flow diagram of a method for determining the remaining life of engine oil, according to a second embodiment of the present invention.

With reference to FIG. 1, the present invention provides a method for determining a remaining life of engine oil in an engine 102. Preferably, the engine 102 is electronically controlled by an Electronic Control Module (ECM) 104. The ECM 104 utilizes a plurality of sensors 105 for determining the correct operating parameters of the engine 102. Electronic control modules of this type are well known in the art and therefore are not further discussed.

The present invention is preferably embodied in the control means 106. In the preferred embodiment, the control means 106 includes a microprocessor based controller 108. It should be noted that the control means 106 and the ECM 104 may be combined in a single microprocessor based controller.

A display means 110 displays information to an operator relating to the remaining life of the engine oil. In the preferred embodiment, the display means 110 includes a display 112. The display 112 may comprise a single LED indicating that the engine oil should be changed or some other display type to illustrate the remaining life of the engine oil.

A signal representing that the oil requires changing or representing the remaining life of the engine oil may additionally or alternatively delivered to a maintenance scheduler or dispatch office so that maintenance can be scheduled.

In one embodiment, the remaining life of engine oil is expressed in terms of a measure of the operating life of the engine. In another embodiment, the remaining life of engine oil is expressed in terms of a percentage (see below).

With reference to FIG. 2, a first embodiment of the present invention will now be discussed. In a first control block 202, a plurality of engine parameters are measured. In the preferred embodiment, the controller 108 receives information directly from the plurality of sensors 105. Additionally, the controller 108 may receive information from the ECM 104. The ECM 104 calculates certain engine parameters based on information from the sensors 105.

In a second control block 204, an estimate of a characteristic of the engine oil is determined as a function of the plurality of engine parameters (see below).

In a third control block 206, the estimate of the characteristic of the engine oil is trended and the remaining life of the engine oil is responsively determined (see below).

Generally, the estimate of the characteristic of the engine oil is trended versus a measure of operation of the engine. For example, the measure of operation may be operating hours of the engine, cycles of the engine, miles traveled, amount of fuel used, or similar measures of the engine's operation.

The characteristic of the engine may be either trended in one dimension or in two dimensions. As discussed below, an estimate may be curve fitted to a function and compared to a threshold. Based on this comparison, a measure of the operation at which the curve fitted function would reach the threshold is determined. This measure of the operation is used to determined the remaining life.

An estimate may also be trended in two dimensions as discussed below.

With reference to FIG. 3, a second embodiment of the present invention will now be discussed. In a fourth control block 302, a plurality of engine parameters are measured.

In a fifth control block 304, an estimate of the soot present in the engine oil is determined as a function of the engine parameters.

In one embodiment, the instantaneous soot per cycle estimate is a function of a rack position, the engine's timing, engine speed, the mean gas temperature, and the fuel to air ratio of the engine. Preferably, the soot estimate is a polynomial function which is based on empirical and/or simulation data. The function may be represented by a look-up table. The accumulated soot estimate is derived from a numeric integration of the instantaneous soot estimate.

In a sixth control block 306, a first estimate of the remaining life of the engine oil is calculated as a function of the soot estimate.

With reference to FIG. 5, the calculation of the first estimate of the remaining life is illustrated. The graph shows the soot estimate versus a measure of the operation of the engine. The measure of the operation of the engine can be any measurement used to measure the operating life of the oil, for example, engine hours, vehicle miles, or fuel used.

Dotted line 502 represents the estimate. The estimates are used to calculate a function representing the level of soot present in the engine oil using conventional curve fitting methods. Dashed line 506 represents a threshold value which represents when the engine oil should be changed. $M_1$ represents the current measure of operation. Line 504 represents the curve fitted function between $M_0$ and $M_1$. The curve fitted function 504 is then set equal to the threshold 506 and the measure of operation is solved for ($M_2$) $M_2$ represents when the threshold would be reached.

Thus, the remaining engine oil life may be represented by:

$$M_2 - M_1 \quad \text{Equation 1A}$$

The remaining oil life in terms of a percentage may be represented by:

$$\frac{M_2 - M_1}{M_2 - M_0} \quad \text{Equation 1B}$$

Typically, today's engine oils contain a dispersant. The dispersant acts to reduce clumping of soot in the engine oil, thus reducing the effect of the soot. In another embodiment, the soot estimate takes into account the level of dispersant present in the oil. In the preferred embodiment, the dispersant is determined by the equation:

$$D(t+\Delta t)=D(t)-DBD(\Delta t)+D_m(\Delta t)-D_c(\Delta t) \quad \text{Equation 2}$$

where $D(t)$ is the dispersant at time t, $DBD(\Delta t)$ represents the dispersant breakdown during engine operation spanning the time interval $\Delta t$, $D_m(\Delta t)$ represents the dispersant present in any makeup oil added during operation, and $D_c(\Delta t)$ represents the dispersant lost by oil consumption. At time, t=0, $D(t)$ is equal to $D_0$, the dispersant level in new oil.

In one embodiment, the sensors 105 include a sensor for measuring the temperature of the engine oil at the top ring groove and the temperature at the sump.

In another embodiment, the temperature at top ring groove is determined using a model. In the preferred embodiment, the model is represented by the equation:

$$TRGT = K_0 + K_1 \cdot X_1 + K_2 \cdot X_2 + K_3 \cdot X_3 + K_4 \cdot X_4 + K_5 \cdot X_5 + K_6 \cdot X_6 + K_7 \cdot X_7 \quad \text{Equation 3}$$

$X_1$ is the fuel to air ratio, $X_2$ is engine speed, $X_3$ is fuel injection timing expressed in geometric degrees, $X_4$ is inlet air temperature, $X_5$ is the square of the fuel to air ratio, $X_6$ is the square of fuel injection timing, $X_7$ is the brake mean effective pressure, and $K_0$–$K_7$ are empirically derived constants. $X_7$ is determined as a function of engine speed and fuel rate.

With reference to FIGS. 10 and 11, the controller 108 measures the time at which the top ring groove temperature and the sump temperature are within predetermined ranges.

For example in FIG. 11, nine temperature ranges are shown between temperatures $T_1$ and $T_{10}$.

FIG. 10 illustrates a histogram of the amount of time spent in each time range. For example, $t1_1$ represents the amount of time the temperature at top ring groove was between temperature $T_1$ $T_2$. Nine temperature ranges are arbitrary. The number of temperatures is generally denoted as N+1. Thus, there will be N temperature ranges.

Referring to FIG. 11, the temperature at the sump will be divided into M ranges. The histogram of FIG. 11 shows eleven ranges between the temperature $t_1$, and $T_{12}$. $T2_r$ represents the amount of time the temperature at sump was in the prescribed range.

Using the histograms of FIGS. 10 and 11, $DBD(\Delta t)$ is determined by:

$$DBD(\Delta t) = \left[ \sum_{k=1}^{N} a_k t1_k + \sum_{k=1}^{M} b_k t2_k \right] \cdot D(t) \quad \text{Equation 4}$$

where $a_k$ and $b_k$ are empirically derived constants.

The level of dispersant added by any engine oil that is added to the engine may be either input by an operator or determined according to a predetermined schedule.

The dispersant consumed by the engine is determined by:

$$D_c(\Delta t)=D(t)*\text{oil consumption rate}*\Delta t \quad \text{Equation 5}$$

where $D(t_1)$ represents the level of dispersant present at the previous time period, the oil consumption rate is a predetermined constant or is a function of engine parameters during $\Delta t$, and $\Delta t$ represents one time period.

With reference to FIG. 6 in an other embodiment, the dispersant estimate and the soot estimate are used to determine the first estimate of the percentage remaining life of the engine oil. As shown, the soot estimate versus the dispersant estimate is graphed. The dotted line 602 represents the actual estimate. Line 604 represents a curve fit of the estimates. The curve fit function 604 may then be solved for a particular engine oil remaining life. The percentage engine oil life may be represented by a series of curves, as shown. Using the soot estimate at which the curve reaches a predetermined oil life, for example 10%, the graph of FIG. 5 may be used to determine the remaining oil life in terms of a measure of the operation.

Returning to FIG. 3, in a seventh control block 308, an estimate of the oxidation of the engine oil is determined as a function of the plurality of engine parameters.

In one embodiment, the oxidation estimate, $O(t)$, is a function of the engine RPM, the temperature at top ring groove, and the temperature at sump. Preferably, the oxidation level is a polynomial based on empirical and/or simulation data. The polynomial may be represented by a look-up table.

In an other embodiment, the oxidation estimate is a function of the engine RPM, the temperature at top ring groove, the temperature at sump and the anti-oxidants remaining in the engine oil.

Anti-oxidant level, $A(t)$, determined in a manner similar to the level of dispersant as described above with respect to FIG. 11 and equations 2, 4 and 5. Thus, oxidation may be determined by:

$$A(\Delta t) = \left[\sum_{k=1}^{N} e_k t1_k + \sum_{k=1}^{M} f_k t2_k\right] * f(A(t)) \quad \text{Equation 6}$$

$$O(\Delta t) = \left[\sum_{k=1}^{N} g_k t1_k + \sum_{k=1}^{M} h_k t2_k\right] * f(A(t)) \quad \text{Equation 7}$$

With reference to FIG. 7, the estimate of the oxidation of the engine oil is illustrated. Dotted line 702 represents the oxidation estimate. In the preferred embodiment, the estimates are curve fitted to a function 704. The curve fit function 704 is then solved for a predetermined threshold 706. $M_1$ represents the current measure of operation and $M_2$ represents the measure of operation at which the curve fit function 704 is equal to the threshold 706. Thus, the second estimate of the percentage remaining life of the engine oil may be determined by equation 1B.

Returning to FIG. 3, in a ninth control block 312, an estimate of the engine oil viscosity is determined as a function of the plurality of engine parameters. In the preferred embodiment, the viscosity estimate is a function of the oxidation estimate, the soot estimate, and fuel dilution. The estimate is a empirically derived polynomial based on empirical or simulated data which may be represented by a look-up table. Fuel dilution represents the contamination of the engine oil by fuel and is determined by:

$$\text{Fuel dilution} = k * \text{fuel leakage} \quad \text{Equation 8}$$

where k is a predetermined constant and fuel leakage is a predetermined function.

With reference to FIG. 9, the viscosity estimate trended over the measure of operation is illustrated. Dotted line 902 represents the viscosity estimate. Solid line 904 represents a curve fitted function of the viscosity estimates. $M_1$ represents the current measure of operation. The curve fit function 904 is set equal to a threshold 1006 and solved for $M_2$. Returning to FIG. 3, in a tenth control block 314, a third estimate of the percentage of the engine oil life is determined as a function of the viscosity estimate. Thus, using FIG. 10, the third estimate of the engine oil life may be calculated by equation 1A. In an eleventh control block 316, an estimate of a total base number of the engine oil is determined as a function of the engine parameters. The total base number represents a measure of the acid neutralizing capacity of the engine oil. In the preferred embodiment, the total base number estimate is represented by a polynomial derived from empirical or simulated data which may be in a look-up table. In the preferred embodiment, the sensors 105 includes an engine coolant temperature sensor and an intake air temperature sensor. The total base number polynomial is a function of engine RPM, engine fuel consumption rate, engine coolant temperature, and intake air temperature.

In a twelfth control block 318, a fourth estimate of the engine oil life is determined as a function of the total base number estimate.

With reference to FIG. 8, calculation of the fourth estimate will now be discussed. Dotted line 802 represents the fourth estimate between $M_0$ and $M_1$. $M_1$ represents the current measure of operation. The fourth estimates are preferably curve fitted to a function. Solid line 804 represents the curve fitted function. The curve fit function 804 is set equal to a predetermined threshold 806 and solved for $M_2$. $M_2$ represents an estimate of the measure of operation when the predetermined threshold will be reached. Thus, the fourth estimate of the percentage remaining life of the engine oil may be calculated using equation 1A.

In a thirteenth control block 320, the first, second, third, and fourth estimates of the percentage remaining life of the engine oil are compared and the percentage remaining life of the engine oil is determined. In the preferred embodiment, the percentage remaining life of the engine oil is determined as the lesser of the first, second, third, and fourth estimates.

With reference to FIG. 4, a third embodiment of the present invention will now be discussed.

In a fourteenth control block 402, a plurality of parameters of the engine 102.

In a fifteenth control block 404, an estimate of the soot present in the engine oil is determined as a function of the parameters (see above).

In a sixteenth control block 406, an estimate of the dispersant level of the engine oil is determined (see above).

In a seventeenth control block 408, a soot value is determined as a function of the soot estimate and the dispersant estimate.

In an eighteenth control block 410, the percentage life remaining of the engine oil is determined as a function of the soot value (see above).

Other aspects, objects, and advantages of this invention can be obtained from a study of the drawings, the disclosure, and the appended claims.

INDUSTRIAL APPLICABILITY

With reference to the drawings and in operation, the present invention is adapted to determining the remaining engine oil life of engine oil.

The method is preferably embodied in a microprocessor controlled controller which receives engine parameter information from sensors and/or another controller. Based on the parameter information, an estimate or one or more characteristics of the oil is calculated. The estimate is trended (see above) to determine an estimate of the remaining life. If more than one estimate of the remaining life is determined, than the shortest estimate is preferably used.

Other aspects, features, and advantages of the present invention may be determined by a study of the specification, drawing and appended claims.

I claim:

1. A method for determining the remaining life of engine oil in an engine, comprising:

measuring a plurality of engine parameters;

determining an estimate of a characteristic of the engine oil as a function of said plurality of engine parameters; and, trending said estimate and responsively determining the remaining life of the engine oil.

2. A method, as set forth in claim 1, wherein the remaining life of engine oil is expressed in terms of a measure of the operating life of the engine.

3. A method, as set forth in claim 1, wherein the remaining life of engine oil is expressed in terms of a percentage.

4. A method, as set forth in claim 1, wherein said trending is with respect to a measure of operation of the engine.

5. A method, as set forth in claim 4, wherein said measure of operation of the engine is operating hours of the engine.

6. A method, as set forth in claim 4, wherein said measure of operation of the engine is fuel consumption.

7. A method, as set forth in claim 4, wherein said measure of operation of the engine is cycles of said engine.

8. A method, as set forth in claim 4, wherein said step of trending includes the steps of:

curve fitting said estimate to a function;

setting said function equal to a predetermined threshold and solving for the remaining life of the engine oil in terms of said measure of operation.

9. A method for determining the remaining life of engine oil in an engine, comprising:

measuring a plurality of engine parameters;

determining an estimate of a first characteristic of the engine oil as a function of said plurality of engine parameters;

calculating a first estimate of the remaining life of the engine oil in response to trending said estimate of said first characteristic;

determining an estimate of a second characteristic of the engine oil as a function of said plurality of engine parameters;

calculating a second estimate of the remaining life of the engine oil in response to trending said estimate of said second characteristic; and, comparing said first and second estimate of the remaining life and responsively determining the remaining life of the engine oil.

10. A method, as set forth in claim 9, wherein the remaining life of engine oil is expressed in terms of a measure of the operating life of the engine.

11. A method, as set forth in claim 9, wherein the remaining life of engine oil is expressed in terms of a percentage.

12. A method, as set forth in claim 9, wherein the remaining life of the engine oil is set equal to the lessor of said first and second estimates.

13. A method for determining the remaining life of engine oil in an engine, comprising:

measuring a plurality of engine parameters;

determining soot estimate as a function of said plurality of engine parameters, said soot estimate being indicative of an amount of soot present in said engine oil;

calculating a first estimate of the remaining life of the engine oil in response to trending of said soot estimate;

determining an oxidation estimate of the engine oil as a function of said plurality of engine parameters, said oxidation estimate being indicative of an amount of oxidation of said engine oil;

calculating a second estimate of the remaining life of the engine oil in response to trending said oxidation estimate;

determining a change in viscosity estimate of the engine oil as a function of said plurality of engine parameters, said viscosity estimate being indicative of a viscosity of said engine oil;

calculating a third estimate of the remaining life of the engine in response to trending said change in viscosity estimate;

determining a total base number estimate of said engine oil as a function of said plurality of engine parameters, said total base estimate being indicative of a measure of acid neutralizing capacity of said engine oil;

calculating a fourth estimate of the remaining life of the engine in response to trending said estimate of said total base number estimate; and, comparing said first, second, third, and fourth estimate of the remaining life and responsively determining the remaining life of the engine oil.

14. A method, as set forth in claim 13, wherein the remaining life of engine oil is expressed in terms of a measure of the operating life of the engine.

15. A method, as set forth in claim 13, wherein the remaining life of engine oil is expressed in terms of a percentage.

16. A method, as set forth in claim 13, wherein the remaining life of the engine oil is set equal to the lessor of said first, second, third, and fourth estimates.

17. A method, as set forth in claim 13, wherein said plurality of engine parameters includes engine rpm, rack position, engine timing, a mean gas temperature and an engine fuel to air ratio.

18. A method, as set forth in claim 13, wherein said step of determining a soot estimate includes the step of:

determining a soot value as a function of said engine rpm, rack position, engine timing, a mean gas temperature and an engine fuel to air ratio;

determining a level of dispersant present in said oil; and, wherein said estimate of soot is a function of said soot value and said level of dispersant.

19. A method, as set forth in claim 13, wherein said plurality of engine parameters includes engine rpm, engine oil temperature at top ring groove, and temperature at sump.

20. A method, as set forth in claim 19, wherein said oxidation estimate is a function of said engine rpm, engine oil temperature at top ring groove, and temperature at sump.

21. A method, as set forth in claim 19, wherein said viscosity estimate is a function of engine rpm, engine oil temperature at top ring groove, and temperature at sump.

22. A method, as set forth in claim 19, wherein said total base number estimate is a function of engine rpm, fuel consumption rate, engine coolant temperature, and intake air temperature.

23. A method for determining the remaining life of engine oil in an engine, comprising:

measuring a plurality of parameters of the engine;

determining a soot estimate as a function of said plurality of parameters, said soot estimate being indicative of an amount of soot present in said oil;

determining a dispersant estimate, said dispersant estimate being indicative of an amount of dispersant remaining in the engine oil;

calculating a soot value as a function of said estimate of soot and said estimate of dispersant; and calculating the remaining life of the engine oil in response to trending said soot value.

24. A method, as set forth in claim 23, wherein the remaining life of engine oil is expressed in terms of a measure of the operating life of the engine.

25. A method, as set forth in claim 23, wherein the remaining life of engine oil is expressed in terms of a percentage.

26. A method, as set forth in claim 25, wherein said trending is with respect to a measure of operation of the engine.

27. A method, as set forth in claim 26 wherein said measure of operation of the engine is operating hours of the engine.

28. A method, as set forth in claim 26, wherein said measure of operation of the engine is fuel consumption.

29. A method, as set forth in claim 26 wherein said measure of operation of the engine is cycles of said engine.

30. A method, as set forth in claim 26, wherein said step of trending includes the steps of:

curve fitting said soot value to a function;

setting said function equal to a predetermined threshold and solving for the remaining life of the engine oil in terms of said measure of operation.

* * * * *